(12) United States Patent
Meconi et al.

(10) Patent No.: US 11,311,495 B2
(45) Date of Patent: Apr. 26, 2022

(54) FIBRE-FREE TRANSDERMAL THERAPEUTIC SYSTEM AND METHOD FOR ITS PRODUCTION

(75) Inventors: Reinhold Meconi, Neuwied (DE); Klaus Schumann, Neuwied (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 1499 days.

(21) Appl. No.: 11/885,716

(22) PCT Filed: Feb. 28, 2006

(86) PCT No.: PCT/EP2006/001840
§ 371 (c)(1),
(2), (4) Date: Apr. 11, 2008

(87) PCT Pub. No.: WO2006/094681
PCT Pub. Date: Sep. 14, 2006

(65) Prior Publication Data
US 2008/0233177 A1    Sep. 25, 2008

(30) Foreign Application Priority Data
Mar. 7, 2005 (DE) .................. 10 2005 010 255.7

(51) Int. Cl.
| | | |
|---|---|---|
| A61K 9/70 | (2006.01) | |
| A61K 31/465 | (2006.01) | |
| A61K 31/196 | (2006.01) | |
| A61K 31/21 | (2006.01) | |
| A61K 31/565 | (2006.01) | |

(52) U.S. Cl.
CPC ............ *A61K 9/7038* (2013.01); *A61K 9/703* (2013.01); *A61K 9/7053* (2013.01); *A61K 9/7061* (2013.01); *A61K 9/7084* (2013.01); *A61K 9/7046* (2013.01); *A61K 31/196* (2013.01); *A61K 31/21* (2013.01); *A61K 31/465* (2013.01); *A61K 31/565* (2013.01)

(58) Field of Classification Search
None
See application file for complete search history.

(56) References Cited

U.S. PATENT DOCUMENTS

| | | | |
|---|---|---|---|
| 4,769,028 A * | 9/1988 | Hoffmann et al. ........... | 424/443 |
| 5,004,610 A | 4/1991 | Osborne et al. | |
| 5,110,599 A * | 5/1992 | Anhauser ................ | A61J 3/10 |
| | | | 424/449 |
| 5,626,866 A | 5/1997 | Ebert et al. | |
| 6,187,322 B1 | 2/2001 | Hille et al. | |
| 6,224,900 B1 | 5/2001 | Hoffmann | |
| 6,264,977 B1 * | 7/2001 | Hoffmann ............. | A61K 9/703 |
| | | | 206/440 |
| 6,586,040 B1 | 7/2003 | Von Falkenhausen | |
| 6,689,379 B1 * | 2/2004 | Bracht ................ | A61K 9/7061 |
| | | | 424/443 |
| 2003/0049308 A1 | 3/2003 | Theobald et al. | |
| 2004/0022836 A1 | 2/2004 | Degen et al. | |
| 2004/0096490 A1 * | 5/2004 | Bracht ................ | A61K 9/7061 |
| | | | 424/449 |
| 2007/0116751 A1 | 5/2007 | Bracht | |

FOREIGN PATENT DOCUMENTS

| | | |
|---|---|---|
| DE | 44 00 769 | 7/1995 |
| DE | 100 53 375 | 1/2000 |
| DE | 101 10 391 | 9/2002 |
| DE | 10110391 | 9/2002 |
| DE | 103 17 692 | 11/2004 |
| EP | 0261402 | 3/1988 |
| EP | 0303025 | 2/1989 |
| RU | 2242971 | 4/2000 |
| WO | WO 00/37058 | 6/2000 |
| WO | WO 2004/091590 | 10/2004 |

OTHER PUBLICATIONS

Product Specification and Test Methods for EUDRAGIT® E100 (Sep. 2004).
Product Information; National Starch & Chemical; DURO-TAK® 2051 (Mar. 1, 2003).
Wolff, et al.; "Development of Processes & Technology for Adhesive-Type Transdermal Therapeutic Systems;" Transdermal Controlled Systemic Medications (Jul. 22, 1987), 365-378.

\* cited by examiner

*Primary Examiner* — Dominic Lazaro
(74) *Attorney, Agent, or Firm* — ProPat, LLC; Cathy R. Moore

(57) ABSTRACT

A transdermal therapeutic system which is free of fibrous constituents, and a method for the production of such a transdermal therapeutic system A preparation containing active substance is applied by a printing method onto the pressure-sensitive adhesive layer of the transdermal therapeutic system.

23 Claims, No Drawings

FIBRE-FREE TRANSDERMAL THERAPEUTIC SYSTEM AND METHOD FOR ITS PRODUCTION

CROSS-REFERENCE TO RELATED APPLICATIONS

This application is a National Stage application of International Application No. PCT/EP2006/001840, filed on Feb. 28, 2006, which claims priority of German application number 10 2005 010 255.7, filed on Mar. 7, 2005.

BACKGROUND OF THE INVENTION

Field of the Invention

The present invention relates to transdermal therapeutic systems (TTSs) and to methods for their production. More particularly, the invention relates to transdermal therapeutic systems which do not contain any fibrous constituents.

The invention further relates to methods for the production of transdermal therapeutic systems wherein the systems are produced without the use of fibrous constituents and are loaded with an active substance by a printing method.

Description of the Prior Art

Transdermal therapeutic systems are systems for the controlled administration of pharmaceutical active substances via the skin. They have been used for some time for treating various diseases, physical as well as mental dysfunctions, complaints and indispositions. Transdermal therapeutic systems are layered products in the form of patches comprising an active substance-impermeable backing layer, at least one active substance-containing reservoir layer or matrix layer, possibly a membrane controlling the rate of active substance release, and a detachable protective layer, which is peeled off the TTS before the latter is used.

To fix a transdermal therapeutic system to the skin and to ensure a controlled administration of the active substance, the TTS is provided with a pressure-sensitive adhesive layer. This pressure-sensitive adhesive layer may be identical to the active substance-containing matrix layer or to the skin-facing active substance-containing layer, but may also be provided in addition thereto if the (skin-facing) active substance-containing layer or the, optionally provided, membrane is not pressure-sensitive adhesive.

Commonly used transdermal therapeutic systems are those which have an active substance-containing reservoir made up of a nonwoven fabric or a paper, that is, of a fibrous material. The nicotine-containing TTS NICOTINELL® may be mentioned as an example for such transdermal therapeutic systems. Such nonwoven-comprising TTSs can be produced, for example, in accordance with the method described in EP 0 261 402 A1.

The backing layer of a TTS must be impermeable to the active substance contained in the TTS in order to prevent undesirable exiting of the active substance from the side of the TTS which is averted from the skin. Materials used for this purpose are, in particular, metal foils, special plastic films as well as composite laminates of these materials. The most frequently used materials are composite laminates of aluminium, and plastic materials such as polyethylene terephthalate. The advantage of these composite laminates is that aluminium foils can be produced at low cost and are impermeable to almost all pharmaceutical active substances. In addition, aluminium foils are impermeable to light, which affords a reliable protection against light, particularly for light-sensitive active substances.

A disadvantage of transdermal therapeutic systems that are provided with a backing layer which comprises an aluminium foil and/or coloured plastic films consists in that they invariably are visually conspicuous on the user's skin. Even if the TTS adhering to the user's skin can be covered by wearing clothes, there is a danger that a TTS having such a backing layer will meet with very little acceptance on the part of the user.

For this reason, TTSs have become recently available which comprise a transparent backing layer and wherein the other layers, too, are permeable to light. In use, these TTSs are almost invisible against the skin to which they adhere since the user's natural skin colour is visible through the TTS.

A method for the production of transdermal therapeutic systems having a transparent backing layer is described in U.S. Pat. No. 5,626,866. In this method, an active substance-containing gel is produced from the active substance, a mixture of different permeation enhancers and a gelatinising agent, and is extruded between two layers of adhesive. Subsequently, individual, active substance-containing patches are punched out from the thus produced active substance-containing laminate.

WO 00/37058 A1 discloses transparent nicotine TTSs exhibiting an opacity index of 17.04% and 19.66%, respectively. They are produced in accordance with the method described in U.S. Pat. No. 5,004,610. SCOTCHPAK® 1220 from the 3M Company, or SARANEX® from the Dow Chemical Company are used as transparent backing layers. Furthermore, a film made of BARANES® may also be used as the transparent backing layer; BARANES® is a graft copolymer material of 73 to 77% acrylonitrile and about 27 to 23% methacrylate, which is produced in the presence of 8 to 18 percent by weight of butadiene/acrylonitrile copolymers containing about 70 percent by weight of butadiene-based polymer units.

To produce nicotine-containing TTSs, the pad printing method known from EP 0 303 025 A1 may be employed. In this process, amounts of 91 mg of solution are printed onto a pressure-sensitive adhesive surface of acrylate using an oval silicone foam rubber pad of a Shore hardness of 6 and a 50 percent by weight solution of nicotine in MIGLYOL® 812.

Finally, from DE 44 00 769, a method for the production of sheet-like administration forms is known wherein a flowable preparation is transferred, with great accuracy, onto a nonwoven-like substrate of defined area by a distributor plate of an application device. The distribution plate is provided with at least one passage and the substrate is brought into contact with said distributor plate.

SUMMARY OF THE PRESENT INVENTION

It was the object of the present invention to provide a transdermal therapeutic system and a method for the production thereof wherein the drawbacks described hereinabove are avoided. More particularly, the aim is to provide a fibre-free TTS as well as a printing method for its production.

This object has been achieved by a transdermal therapeutic system which can do without fibrous constituents.

DETAILED DESCRIPTION OF THE PRESENT INVENTION

In a preferred embodiment, the TTS according to the invention comprises an active substance-impermeable, light-permeable backing layer, at least one light-permeable pressure-sensitive adhesive layer, onto which an active substance-containing preparation has been applied, and a detachable protective layer. The TTS is free of fibrous constituents. Any further, optionally present reservoir layers or matrix layers are also free of fibres and permeable to light. Hence, this embodiment of the TTS according to the invention consists exclusively of light-permeable layers and is free of fibrous constituents.

A light-permeable layer is understood to be a transparent or translucent layer. A transparent layer allows light to pass through it almost unhindered, whereas a translucent layer allows most of the light to pass through but scatters the light diffusely. The layers of a preferred embodiment of the inventive TTS are clear (totally) transparent. However, at least one of the layers of the inventive TTS may also be tinted or—due to portions of organic and/or inorganic colour pigments—coloured such that the degree of their transparency depends on the wavelength of the light. In this way, totally or partially light-impermeable TTSs can be provided.

In another preferred embodiment, the inventive TTS is skin-coloured. The TTS is thereby less conspicuous. As a rule, users indeed prefer inconspicuous patches so that other people are less likely to notice and find out about the user's need for treatment.

To produce skin-coloured TTSs, the backing layer may be lacquered in a skin colour. Although it is not possible to provide the backing layer with a uniform opaque skin colour tone that will correspond to all skin colour tones present in the world population. But otherwise identical active substance patches can be provided with differently coloured backing layers, each colour being adapted to one of the skin colour tones present in the world population so that the patch will be acceptable to a rather large number of users whose skin colour differs only in nuance.

A fibrous constituent in the sense of the present invention is understood to mean relatively long, thin and flexible structures of natural or synthetic material. The fibrous constituents of natural materials include, for example, plant fibres, animal fibres and mineral fibres. Plant fibres, such as bast, cotton, hemp, coconut, linen, kapok or ramie, generally consist of cellulose. The animal fibres include silk and hair (wool). A naturally occurring mineral fibre is asbestos. The synthetic fibres include fibres of perlon, nylon, but also synthetic silk, glass fibres and carbon fibres. A number of fibres together form larger structures. Thus, textile fibres may jointly form a thread, a rope or a fabric. Cellulose fibres, for example, are used for the manufacture of paper and textiles. In the field of transdermal therapeutic systems, fibres are mainly used in the form of nonwovens, paper, long-fibre paper and textile sheet material having a supporting and/or distributing function or having a reservoir function.

The pressure-sensitive adhesive layer and/or the optionally present reservoir layer(s) or matrix layer(s) of the TTS according to the invention may comprise a material which is selected from a group consisting of pressure-sensitive adhesive polymers based on acrylic acid and/or methacrylic acid as well as esters thereof, polyacrylates, isobutylene, polyvinyl acetate, ethylene-vinyl acetate, natural and/or synthetic rubbers, for example acrylonitrile-butadiene rubber, butyl rubber or neoprene rubber, styrene-diene copolymers such as styrene-butadiene block copolymers, and hot-melt adhesives, or which is produced on the basis of pressure-sensitive adhesive silicone polymers or polysiloxanes.

Preferably, the material comprising the pressure-sensitive adhesive layer is selected from the group comprising cationic copolymers based on dimethylaminoethyl methacrylate and neutral methacrylic esters, for example EUDRAGIT® E 100, and neutral copolymers based on butyl methacrylate and methyl methacrylates, for example PLASTOID® B.

For transparent or translucent TTSs, the pressure-sensitive adhesive layer of the TTS must be permeable to light. The pressure-sensitive adhesive layer is preferable clear-transparent, but can also be tinted or coloured.

The backing layer, which is connected to the pressure-sensitive adhesive layer or to a reservoir layer or matrix layer, which is optionally provided in addition thereto, is impermeable to the active substance to be administered with the respective TTS and has occlusive properties. The backing layer of the TTS according to the invention may be permeable to light. It is free of fibrous constituents. In a particularly preferred embodiment, the backing layer is colourless, that is, it is clear-transparent. However, the light-permeable backing layer may also be tinted, or it may be coloured due to proportions of organic and/or inorganic colour pigments contained therein, so as to be totally or partially impermeable to light.

In other embodiments, the TTS according to the invention may be entirely or partially impermeable to light. It is particularly preferred that the TTS be skin-coloured, for example by providing a backing layer that is lacquered in a skin colour.

For the backing layer, any materials may be used that meet the aforementioned requirements.

Such materials may, for example, be polymers from the group comprising polyethylene terephthalate, plasticised vinyl acetate-vinyl chloride copolymers, nylon, ethylene-vinyl acetate copolymers, plasticized polyvinyl chloride, polyurethane, polyvinylidene chloride, polypropylene, polyethylene or polyamide.

The transdermal therapeutic system according to the invention contains at least one pharmaceutically active substance which can be delivered to a person via the skin. Suitable as the active substance are, in principle, any transdermally applicable pharmaceutical active substances which can be contained, as single active substances or in combination with one another, in a TTS and which can be administered transdermally. At room temperature, the active substance may be a solid but may also be liquid. Both non-volatile active substances such as fentanyl, but also volatile active substances such as nicotine are suitable for administration with the TTS according to the invention.

Further active substances, which may be contained in a TTS according to the invention, are, for example, alprostadil, buprenorphine, clonidine, dexamethasone, dextroamphetamine, diclofenac, dihydrotestosterone, estradiol (also in combination with androgenic or progestinic active substances), fentanyl, flurbiprofen, lidocaine, methylphenidate, nitroglycerin, rotigotin, salicylic acid, scopolamine, testosterone and tulobuterol.

The TTS according to the invention is manufactured without use of fibrous constituents, by applying the active substance by a suitable printing method onto the fibre-free pressure-sensitive adhesive layer.

As a printing method, the pad printing method is particularly suitable for loading the TTS with an active substance. In this process, a flowable active substance preparation is transferred onto the pressure-sensitive adhesive layer by using a pad. This printing method is carried out at a constant temperature, thereby achieving high dosage accuracy.

In a further suitable printing method, which, surprisingly, is suitable for the production of the transdermal therapeutic systems according to the present invention, the preparation containing the active substance is transferred, by a distributor plate of an application device, onto the fibre-free pressure-sensitive adhesive layer.

To manufacture the TTS according to the invention, initially a fibre-free, preferably transparent, pressure-sensitive adhesive layer, located on an active substance-impermeable carrier layer, may be produced. Individually dosed portions of a preparation containing active substance are applied to the pressure-sensitive adhesive layer by employing a suitable printing method.

In a further step, the backing layer is applied to the pressure-sensitive adhesive layer, which is provided with the active substance-containing preparation, in such a way that the active substance-containing preparation can no longer exit at that side of the resultant composite laminate. Finally, individual TTSs are produced from the thus-obtained intermediate product by cutting and/or punching. The intermediate product, as the case may be, may comprise further reservoir or matrix layers and/or an active substance release-controlling membrane which likewise is free of fibres and which, if required, is permeable to light. In the finished TTS, the active substance-impermeable carrier layer represents the detachable layer.

However, after applying the active substance-containing preparation, but before applying the backing layer, it is also possible to singularise TTSs from the composite laminate, which has by then been formed and to subsequently cover the TTSs with a backing layer.

Thus, the method for the production of a transdermal therapeutic system is characterised in that:
- an active substance-impermeable carrier layer or an optionally present reservoir layer or matrix layer is provided with a fibre-free pressure-sensitive adhesive layer;
- individually dosed portions of a flowable, active substance-containing preparation are applied onto the pressure-sensitive adhesive layer by a printing method; and
- in a further step, an active substance-impermeable, fibre-free backing layer is applied to the pressure-sensitive adhesive layer, which has been provided with the active substance-containing preparation.

The TTSs are able to be singularised, by cutting and/or punching, prior to or following the application of the active substance-containing preparation, from the composite laminate which has by then been formed.

To produce the TTS according to the present invention, the active substance must be present in a flowable state which permits single dosage by a suitable printing method. In the case of active substances which under normal manufacturing conditions are present as solids, this is done by adding suitable solvents as well as, as the case may be, by adding further auxiliary substances by which the viscosity of the active substance preparation can be adjusted. Suitable as solvents are, in principle, any of the conventional organic solvents, such as ethanol, isopropyl alcohol, heptane, hexane, ethyl acetate, petroleum ether, benzine, acetone, glycerol, DEET (N,N-diethyl-3-methylbenzamide), THF as well as many oils, for example silicone oil, paraffin, triglycerides, neutral oil or plant oils.

Liquid active substances may be applied directly by the printing method. Usually, however, liquid active substances, too, are employed in the form of a liquid that exhibits the desired viscosity as a result of an addition of suitable solvents and/or auxiliary substances.

The viscosity of the active substance-containing preparation to be used as the printing medium is preferably in the range of 10 to 100 dPa's, especially preferably in a range of 15 to 25 dPa's.

By performing the printing method at a temperature which is as constant as possible, it is possible to achieve a high accuracy of dosage. The printing method is preferably performed at room temperature, but can also be carried out at lower or higher temperatures.

In a preferred manufacturing process, the active substance is mixed with a solution, suspension or dispersion of a polymer that is also a constituent of the fibre-free pressure-sensitive adhesive layer of the TTS to be produced. In that case, the viscosity of the mixture can be adjusted by adjusting the ratio of active substance to pressure-sensitive adhesive such that the mixture can be employed as a printing medium. This mixture is then used as the printing medium. Preferred polymers for the production of the printing medium are cationic polymers based on dimethylaminoethyl methacrylate and neutral methacrylic esters, such as EUDRAGIT® E 100, and neutral copolymers based on butyl methacrylate and methyl methacrylates, for example PLASTOID® B.

The method is especially well suited for active substances which at room temperature are liquid and/or highly volatile so that dissolving the active substance in the adhesive and drying at temperatures between 60 and 100° C. is not possible because the active substance is too highly volatile or too thermosensitive. These active substances include, for example, nicotine, nitroglycerin, bupropion, but also essential oils such as menthol, camphor, turpentine, or oils from mountain pine, peppermint, spearmint, lemon or cloves, as well as almost all of the polypeptides and proteins. DEET and DMSO also belong to the highly volatile substances.

In a particularly preferred method, EUDRAGIT® E 100 is dissolved in nicotine, and this active substance solution is used as the printing medium. The quantity ratio of nicotine to EUDRAGIT® is preferably 1:1 to 1:3, especially preferably 1.4:1 up to 2.4:1.

Other active substances that are suitable for being applied with this method are alprostadil, buprenorphine, clonidine, dexamethasone, dextroamphetamine, diclofenac, dihydrotestosterone, estradiol (also in combination with androgenic or progestinic active substances), fentanyl, flurbiprofen, lidocaine, methyl phenidate, nitroglycerin, rotigotin, salicylic acid, scopolamine, testosterone and tulobuterol.

Example

A pressure-sensitive adhesive mass, consisting of 2.0825 kg of a 40% solution of a self-crosslinking acrylate polymer (of 2-ethylhexyl acrylate, vinyl acetate, acrylic acid and titanium chelate ester; commercially available under the designation DUROTAK® 280-2416 (National Starch & Chemical B.V.)) in a mixture of acetic acid ethyl ester, ethanol, hexane and menthol, 147 g of an acrylic resin of dimethylaminoethyl methacrylate and neutral methacrylic esters (EUDRAGIT® E 100 from the Röhm-Pharma company), as well as 20 g of a mixed-acidic triglyceride of fractionated coconut fatty acids $C_8$-$C_{10}$ (MIGLYOL® 812 from the Dynamit Nobel company) was applied onto a protective layer which had been vapour-coated on one side and rendered adhesive on both sides. Subsequently, the solvent was evaporated at 50 to 80° C. A pressure-sensitive adhesive layer having a weight per unit area of approximately 300 g/m² was obtained. From the thus-produced pressure-sensitive adhesive layer, circular blanks of a diameter of 65 mm were punched, and the projecting margins were removed.

A dose of 102 mg nicotine was applied onto the pressure-sensitive adhesive layer of each circular blank as active substance preparation in the form of a solution (140 g of nicotine in 100 g EUDRAGIT® E 100). To this end, a pad printer, with a steel printing plate, having a round depression of 39 mm and an etching depth of 240 µm as the printing style, was used for printing the blanks. As pad, an oval silicone foam rubber pad, with a Shore hardness of 6, was used. The nicotine-EUDRAGIT® solution was used as the printing medium, and circular layers of said printing medium were placed on the blanks by using the pad.

A transparent, 15-µm-thick polyester film was immediately laminated, as a nicotine-impermeable backing layer, onto the "patches" produced in the above-described manner. Subsequently, the finished products were sealed in four-side-sealed bags made of a known composite packaging material (BAREX®).

What has been described above are preferred aspects of the present invention. It is of course not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, combinations, modifications, and variations that fall within the spirit and scope of the appended claims.

The invention claimed is:

1. A three-layered transdermal therapeutic system (TTS) consisting of an active substance-impermeable backing layer, a pressure-sensitive adhesive layer as a reservoir or matrix onto which a flowable active substance-containing preparation has been applied, and a detachable protective layer,
    wherein said transdermal therapeutic system is free of fibrous constituents and is permeable to light, and the flowable active substance-containing preparation consists of (i) a cationic polymer which is also a constituent of said pressure-sensitive adhesive layer and (ii) active substance;
    wherein said backing layer is free of fibers and is permeable to light;
    wherein said pressure-sensitive adhesive layer is free of fibers and is permeable to light; and
    and said flowable active substance-containing preparation was applied by a printing method comprising the step of transferring the flowable active substance-containing preparation onto the fiber-free pressure-sensitive adhesive layer by a distributor plate of an application device, said distributor plate being provided with at least one passage,
    and the pressure sensitive layer consists of (i) said cationic polymer; (ii) self-crosslinking acrylate polymer; (iii) oil selected from silicone oil, paraffin, triglycerides, neutral oil or plant oils; and (iv) diffused active substance.

2. The transdermal therapeutic system according to claim 1, wherein said backing layer is a material selected from the group consisting of polyethylene terephthalate, plasticised vinyl acetate-vinyl chloride copolymers, nylon, ethylene-vinyl acetate copolymers, plasticized polyvinyl chloride, polyurethane, polyvinylidene chloride, polypropylene, polyethylene and polyamide.

3. The transdermal therapeutic system according to claim 1, wherein said cationic polymer consists of dimethylaminoethyl methacrylate and neutral methacrylic esters; and said active substance is nicotine.

4. The transdermal therapeutic system according to claim 1, wherein said active substance is a liquid or a solid at room temperature.

5. The transdermal therapeutic system according to claim 1, wherein said active substance of said active substance-containing preparation is selected from the group consisting of alprostadil, buprenorphine, bupropion, clonidine, dexamethasone, dextroamphetamine, diclofenac, dihydrotestosterone, estradiol, estradiol in combination with androgenic active substances, estradiol in combination with progestinic active substances, fentanyl, flurbiprofen, lidocaine, methylphenidate, nicotine, nitroglycerin, rotigotin, salicylic acid, scopolamine, testosterone, tulobuterol and essential oils.

6. The transdermal therapeutic system according to claim 1, wherein the application of the active substance-containing preparation gives rise to an active substance loading gradient within the inventive pressure-sensitive adhesive layer.

7. The transdermal therapeutic system according to claim 1, wherein the active substance-containing preparation has a viscosity ranging from 10 to 100 dPa·s.

8. The transdermal therapeutic system according to claim 1, wherein said active substance is nicotine and said triglyceride is a mixed-acidic triglyceride of fractionated coconut fatty acids $C_8$-$C_{10}$.

9. A method for producing a transdermal therapeutic systems as claimed in claim 1 comprising the steps of:
    providing an active substance-impermeable layer or an optionally present reservoir layer or matrix layer with a fibre-free pressure-sensitive adhesive layer;
    by a printing method, applying individually dosed portions of a flowable, active substance-containing preparation onto the pressure-sensitive adhesive layer, said flowable active substance-containing preparation consists of (i) a cationic polymer which is also a constituent of the fibre-free pressure-sensitive adhesive layer and (ii) active substance, to form a composite laminate; and
    in a further step, applying an active substance-impermeable, fibre-free backing layer onto the pressure-sensitive adhesive layer, said pressure-sensitive adhesive layer having been provided with the active substance-containing preparation;
    said pressure sensitive layer consists of (i) said cationic polymer; (ii) self-crosslinking acrylate polymer; (iii) oil selected from silicone oil, paraffin, triglycerides, neutral oil or plant oils and (iv) diffused active substance;
    said transdermal therapeutic systems being able to be singularised by at least one of cutting and punching prior to or following said step of applying the active substance-containing preparation, from the composite laminate having been formed by said last-mentioned step of applying the active substance-containing preparation; and
    said printing method is a method comprising the step of transferring the active substance-containing preparation onto the fibre-free pressure-sensitive adhesive layer by a distributor plate of an application device, said distributor plate being provided with at least one passage.

10. The method according to claim 9, wherein said printing method is a pad printing method.

11. The method according to claim 1, wherein said cationic polymer is selected from the group consisting of copolymers based on dimethylaminoethyl methacrylate and neutral methacrylic esters.

12. The method according to claim 1, wherein said backing layer is selected from the group consisting of completely light-permeable backing layers, partially light-permeable backing layers, light-impermeable backing layers and skin-coloured backing layers.

13. The method according to claim 12, wherein said backing layer is lacquered skin-coloured.

14. The method according to claim 1, wherein said backing layer is a material selected from the group consisting of polyethylene terephthalate, plasticised vinyl acetate-vinyl chloride copolymers, nylon, ethylene-vinyl acetate copolymers, plasticized polyvinyl chloride, polyurethane, polyvinylidene chloride, polypropylene, polyethylene and polyamide.

15. The method according to claim 1, wherein said active substance is a liquid or solid at room temperature.

16. The method according to claim 1, wherein said active substance is selected from the group consisting of alprostadil, buprenorphine, bupropion, clonidine, dexamethasone, dextroamphetamine, diclofenac, dihydrotestosterone, estradiol, estradiol in combination with androgenic active substances, estradiol in combination with progestinic active substances, fentanyl, flurbiprofen, lidocaine, methylphenidate, nicotine, nitroglycerin, rotigotin, salicylic acid, scopolamine, testosterone, tulobuterol and essential oils.

17. A four-layered transdermal therapeutic system (TTS) consisting of:
    an active substance-impermeable backing layer, said active substance-impermeable backing layer being free of fibers and being permeable to light;
    a pressure-sensitive adhesive layer as a reservoir or matrix onto which a flowable active substance-containing preparation has been applied, said pressure-sensitive adhesive layer being free of fibers and being permeable to light;
    a detachable protective layer, wherein said transdermal therapeutic system is free of fibrous constituents and is permeable to light,
    the flowable active substance-containing preparation consists of (i) a cationic polymer which is also a constituent of said pressure-sensitive adhesive layer and (ii) active substance;
    the pressure sensitive layer consists of (i) said cationic polymer; (ii) self-crosslinking acrylate polymer; (iii) triglyceride or plant oil; and (iv) diffused active substance, and
    a further reservoir layer or matrix layer, said further reservoir layer or matrix layer being free of fibres and consisting of a material which is selected from the group consisting of polyacrylates, isobutylene, polyvinyl acetate, ethylene-vinyl acetate, hot-melt adhesives and at least one of natural or synthetic rubbers.

18. The transdermal therapeutic system according to claim 17, wherein said material is selected from the group consisting of cationic copolymers consisting of dimethylaminoethyl methacrylate and neutral methacrylic esters; and said active substance is nicotine.

19. A fiber-free, light permeable three-layered transdermal therapeutic system (TTS) consisting of:
    a fiber-free, light permeable active substance-impermeable backing layer having a thickness of about 15 µm;
    a fiber-free, light permeable pressure-sensitive adhesive layer as a reservoir or matrix directly adjacent to said backing layer,
    a flowable active substance-containing preparation between said pressure-sensitive adhesive layer and said backing layer, said flowable active substance-containing preparation alone providing said active substance, and
    a detachable protective layer directly adjacent to said pressure-sensitive adhesive layer on the side opposite that adjacent to said backing layer;
    wherein said transdermal therapeutic system is free of fibrous constituents and is permeable to light, and wherein the flowable active substance-containing preparation consists of (i) a first pressure-sensitive adhesive cationic polymer, said first pressure-sensitive cationic polymer also being a constituent of said pressure-sensitive adhesive layer and (ii) active substance,
    the flowable active substance-containing preparation is applied onto the fibre-free pressure-sensitive adhesive layer by a distributor plate of an application device, said distributor plate being provided with at least one passage,
    and the pressure sensitive layer consists of (i) said cationic polymer; (ii) self-crosslinking acrylate polymer; (iii) triglyceride and (iv) diffused active substance.

20. The transdermal therapeutic system according to claim 19, wherein said active substance is a liquid at room temperature, said first pressure-sensitive adhesive cationic copolymer consists of dimethylaminoethyl methacrylate and neutral methacrylic esters, and said active substance is nicotine.

21. The transdermal therapeutic system according to claim 19, wherein said self-crosslinking acrylate adhesive polymer and first pressure-sensitive adhesive cationic polymer are present at about a 5.7:1 ratio and said active substance is nicotine.

22. The transdermal therapeutic system according to claim 19, wherein said triglyceride is a mixed-acidic triglyceride of fractionated coconut fatty acids $C_8$-$C_{10}$.

23. The transdermal therapeutic system according to claim 20, wherein
    said active substance is nicotine, and
    said pressure-sensitive adhesive layer consists of self-crosslinking acrylate adhesive, the first pressure-sensitive adhesive polymer, diffused active substance and a mixed-acidic triglyceride of fractionated coconut fatty acids $C_8$-$C_{10}$.

* * * * *

UNITED STATES PATENT AND TRADEMARK OFFICE
CERTIFICATE OF CORRECTION

| | | |
|---|---|---|
| PATENT NO. | : 11,311,495 B2 | Page 1 of 1 |
| APPLICATION NO. | : 11/885716 | |
| DATED | : April 26, 2022 | |
| INVENTOR(S) | : Meconi et al. | |

It is certified that error appears in the above-identified patent and that said Letters Patent is hereby corrected as shown below:

In the Claims

Column 9, in Claims 11, 12, 14, 15 and 16, delete "according to claim 1" and insert --according to claim 9--

Signed and Sealed this
Thirtieth Day of August, 2022

Katherine Kelly Vidal
*Director of the United States Patent and Trademark Office*